United States Patent
Deininger

(10) Patent No.: US 10,950,424 B2
(45) Date of Patent: Mar. 16, 2021

(54) METHOD FOR MONITORING THE QUALITY OF MASS SPECTROMETRIC IMAGING PREPARATION WORKFLOWS

(71) Applicant: Bruker Daltonik, GmbH, Bremen (DE)

(72) Inventor: Sören-Oliver Deininger, Leipzig (DE)

(*) Notice: Subject to any disclaimer, the term of this patent is extended or adjusted under 35 U.S.C. 154(b) by 782 days.

(21) Appl. No.: 15/714,280

(22) Filed: Sep. 25, 2017

(65) Prior Publication Data

US 2019/0096648 A1 Mar. 28, 2019

(51) Int. Cl.
| | |
|---|---|
| H01J 49/04 | (2006.01) |
| G01N 33/68 | (2006.01) |
| G01N 33/50 | (2006.01) |
| H01J 49/00 | (2006.01) |
| H01J 49/16 | (2006.01) |
| H01J 49/40 | (2006.01) |

(52) U.S. Cl.
CPC ...... *H01J 49/0418* (2013.01); *G01N 33/5044* (2013.01); *G01N 33/6848* (2013.01); *H01J 49/0004* (2013.01); *H01J 49/164* (2013.01); *H01J 49/40* (2013.01); *G01N 33/6851* (2013.01)

(58) Field of Classification Search
CPC ........... G01N 33/5044; G01N 33/6848; G01N 33/6851; H01J 49/0418; H01J 49/164; H01J 49/40; H01J 49/0004
See application file for complete search history.

(56) References Cited

U.S. PATENT DOCUMENTS

| | | | |
|---|---|---|---|
| 7,873,478 B2 * | 1/2011 | Suckau | G01N 33/483 702/19 |
| 9,768,001 B2 * | 9/2017 | Cooper | G01N 30/8665 |
| 9,970,932 B2 * | 5/2018 | Woodbury | G01N 33/54366 |
| 10,330,613 B2 * | 6/2019 | Fischer | G01N 24/08 |
| 2006/0282221 A1 * | 12/2006 | Shah | G06K 9/00127 702/19 |
| 2009/0325222 A1 * | 12/2009 | Agar | G01N 1/30 435/40.5 |
| 2011/0280455 A1 * | 11/2011 | Alexandrov | H01J 49/0036 382/128 |
| 2013/0274143 A1 * | 10/2013 | Emanuele, II | H01J 49/164 506/12 |
| 2016/0041158 A1 * | 2/2016 | Woodbury | G01N 33/54366 506/9 |
| 2018/0259510 A1 * | 9/2018 | Woodbury | G01N 33/54366 |

(Continued)

OTHER PUBLICATIONS

M. Reid Groseclose et al., "A Mimetic Tissue Model for the Quantification of Drug Distributions by MALDI Imaging Mass Spectrometry", Analytical Chemistry, vol. 85 No. 21, p. 10099-10106, Oct. 7, 2013.

(Continued)

*Primary Examiner* — Wyatt A Stoffa
(74) *Attorney, Agent, or Firm* — Benoit & Côté Inc.

(57) ABSTRACT

The invention relates to a method for monitoring a quality of preparation workflows of analytical tissue sections for mass spectrometric imaging using a control sample to be processed and measured alongside the analytical tissue sections on the same sample support and ascertaining if characteristics of the control sample measurement fit into a range of characteristics of separate reference measurements from the same type of control sample.

20 Claims, 6 Drawing Sheets

(56) References Cited

U.S. PATENT DOCUMENTS

2019/0096650 A1* 3/2019 Deininger ............ H01J 49/0004
2019/0187151 A1* 6/2019 Leblanc ................. G01N 33/48

OTHER PUBLICATIONS

John G. Swales et al., "Spatial Quantitation of Drugs in tissues using Liquid Extraction Surface Analysis Mass Spectrometry Imaging", Scientific Reports, vol. 6, No. 1., Nov. 24, 2016.

Rzagalinski Ignacy et al., "Quantification of low molecular weight compounds by MALDI imaging mass spectrometry—A tutorial review", Biochimica et Biophysica Acta (BBA)—Proteins & Proteomics, Elsevier, Netherlands, vol. 1865, No. 7, p. 726-739, Dec. 22, 2016

Huber K. et al., "A rapid ex vivo tissue model for optimising drug detection and ionisation in MALDI imaging studies", Histochemistry and Cell Biology, Springer, Berlin, DE, vol. 142, No. 4, May 14, 2014.

Andrew Palmer et al., Using collective expert judgements to evaluate quality measures of mass spectrometry images, Bioinformatics, vol. 31, No. 12, Jun. 13, 2015.

* cited by examiner

METHOD FOR MONITORING THE QUALITY OF MASS SPECTROMETRIC IMAGING PREPARATION WORKFLOWS

BACKGROUND OF THE INVENTION

Field of the Invention

The invention relates to the field of mass spectrometry imaging (MSI), in particular using MALDI (matrix assisted laser desorption/ionisation) as ionisation technique and time-of-flight (TOF) analysers.

Description of the Related Art

Mass spectrometric imaging, the MALDI variant of which has been pioneered by Richard M. Caprioli, see for instance U.S. Pat. No. 5,808,300 the content of which is incorporated herein by reference in its entirety, is a technique that is increasingly used in tissue based research, and there is the expectation that the technique can also contribute to the diagnosis or classification of tissue. Existing methods for tissue diagnosis, such as the microscopic analysis of chemically stained or immune-stained tissue sections are carried out by human inspection and have therefore an undesired subjective component. Since mass spectrometric profiles can be objectively measured, there is the expectation that MSI can help with the objective classification or diagnosis of tissue.

Mass spectrometric profiling is already used in the identification of microorganisms, see for example C. Fenselau et al., Mass Spectrometry Reviews, 2001, 20, 157-171. For this identification, the microorganisms are cultured, then prepared for mass spectrometry and measured in a mass spectrometer. The resulting mass spectra are then compared to reference spectra of a spectral library, the presence of characteristic mass signals and the shape of the spectra is investigated, and scores for the agreement between the measured spectrum and the reference spectra are given. If no related reference spectrum is found in the library, then the score is low, effectively reporting a non-identification. In the case of microorganisms, this approach works because the resulting mass spectra are largely independent of sample preparation conditions. This approach has been commercialised, for example, with the MALDI Biotyper® system marketed by Bruker Daltonics Inc. (Billerica, Mass.).

In the case of mass spectrometry based tissue classification, such as for the discrimination of diseased tissue from healthy tissue or of different types of diseased tissue, a simple library approach like for the microorganisms generally does not work. The reason for this is that, in relevant tissue, the contribution of different cell types has to be anticipated; in other words, "pure" cell populations over larger areas will rarely be seen. In the analysis of solid tumours, for instance, tumour cells will make up for only a certain percentage, with probably different influences on inflammation processes, such as the infiltration of lymphocytes surrounded by connective tissue. All of these different cells will contribute their own mass spectrometric profile, and in many applications the spatial resolution of the MSI measurement is not sufficient to resolve individual cells. There is also biological variation since different patients and also different tumours have different genetic backgrounds that will be reflected in the mass spectrometric phenotype.

Those of skill in the art will further appreciate that tissue specimens to be investigated with mass spectrometry imaging are much more susceptible to the exact sample preparation and processing conditions so that slight deviations and larger aberrations from the foreseen protocols can (and frequently do) lead to significantly altered and distorted images of the analytes of interest. It goes without saying that these undesired processes complicate meaningful analysis and, especially, comparability of such data.

In view of the foregoing, there is still a need for monitoring the accurateness of MSI sample preparation workflows and, in particular, recognising false classifications that are caused by unexpected and undesired variations in such sample preparation workflows for mass spectrometric imaging.

SUMMARY OF THE INVENTION

The disclosure relates most generally to a method for monitoring a quality of preparation workflows of an analytical tissue section for mass spectrometric imaging.

The most basic principle underlying the invention is to prepare and measure a suitable control sample alongside with an analytical tissue section to be investigated (or a plurality of such analytical tissue sections). In so doing, it is possible to monitor accurate processing of the tissues in the sample preparation steps, using multivariate feature analysis methods, by virtue of the particular mass signal characteristics in the control samples. These characteristics are identified in a multitude of separate measurements of specimens from the same control sample type, which undergo substantially the same preparation conditions in order to establish comparability.

The invention generally relates to a method for monitoring a quality of sample preparation workflows of an analytical tissue section for mass spectrometric imaging, comprising providing a sample support suitable for mass spectrometric imaging, such as a flat conductive plate (e.g. stainless steel plate, conductive layer-coated glass/ceramic plate and the like); depositing the analytical tissue section(s) and a control sample on the sample support, wherein the control sample encompasses tissue which is preferably substantially homogeneous (and where a tissue can be understood to be an ensemble of similar cells from the same origin that together carry out a specific function); jointly preparing the analytical tissue section and the control sample for analysis under predetermined conditions, which conditions may comprise exposure of the control sample and the analytical tissue section(s) to at least one of liquid and wet chemistry; acquiring (spatially resolved) mass spectra from the control sample and acquiring spatially resolved mass spectra from the analytical tissue section in a same measurement run; subjecting the mass spectra of the control sample to multivariate feature analysis; ascertaining if a result of the multivariate feature analysis fits into a range of outcomes established by subjecting a set of reference control mass spectra, which are obtained from control samples of a same type that have been prepared (previously) under substantially the same predetermined conditions, to the same multivariate feature analysis; and tagging a mass spectrometric image produced from the spatially resolved mass spectra of the analytical tissue section with a result of the ascertaining, such as chosen from one of the categories "trustworthy" (good quality), "moderately trustworthy", "questionable" and "untrustworthy" (bad quality).

In various embodiments, at least one of a kidney section, liver section, muscle section and a section from a tissue surrogate comprising cultured cells can be used as the control sample. These exemplary tissue types have the advantage that they can be supplied in large quantities at a quite consistent quality, which may be beneficial when larger batches of analytical tissue are to be examined mass spectrometrically. While each analytical tissue section has to be scanned pixel-by-pixel in any case in order to preserve the position information of the analytes and facilitate the drawing of a distribution map, the mass spectra acquired from the control sample do not necessarily have to be spatially resolved, in particular not so when a control sample comprising solely one homogeneous tissue type is used. In some cases, however, it can be expedient to also acquire spatially resolved mass spectra from the control sample, for example, in order that a sample support plate carrying the control sample as well as the analytical tissue section(s) can be handled with uniform rastering and complicated switching between different rastering modes can be avoided.

In various embodiments, the multivariate feature analysis of the mass spectra from the current control sample and the reference control mass spectra may be carried out one of separately and jointly, and the ascertaining can comprise checking if the results of the multivariate feature analysis fall into a same region of a multivariate feature space. In some variants, the separate multivariate feature analyses can encompass using at least one of a single-class support vector machine and density estimator. In other variants, the joint multivariate feature analysis can encompass using at least one of principal component analysis, k-means clustering and hierarchical clustering. It will be appreciated that skilled practitioners in this field are familiar with this kind of mathematical algorithms so that it is not necessary to describe them here in detail. The joint multivariate feature analysis may furthermore employ solely a randomly chosen subset of the reference control mass spectra in order to shorten calculation time.

In various embodiments, the predetermined conditions under which the control samples of the same type for the reference control mass spectra have been prepared can comprise using different batches of same chemical reagents and different embodiments of a same instrument type or model. By virtue of these slight variations of a particular preparation protocol, it is possible to account for minor unforeseen variations in the workflow that may happen in everyday laboratory routine to ensure that the acceptance region, which indicates trustworthy (good quality) results, is not defined too narrow.

In preferred embodiments, the method can further comprise obtaining the reference control mass spectra from reference control samples of the same (preferably homogeneous) type which are measured alongside training tissue sections each prepared together with the corresponding control sample on a same sample support, wherein the measurements from the training tissue sections are used to define a tissue-specific analytical classifier based on characteristic mass signal profiles. The analytical classifier may be applied to (regions of interest in) the spatially resolved mass spectra from the analytical tissue section of the same tissue type as the training tissue sections. Defining the analytical classifier can comprise using at least one of principal component analysis based models, a linear discriminant analysis, support vector machines, genetic algorithms, neuronal networks, decision trees, and random forests. It will be appreciated that skilled practitioners in this field are familiar with this kind of mathematical algorithms so that it is not necessary to describe them here in detail.

Preferably, a first portion of the mass spectra from the control sample is acquired before the acquisition of the spatially resolved mass spectra from the analytical tissue section (to be classified) and a second portion of the mass spectra from the control sample thereafter, and wherein the mass spectrometric image or a classification found by applying an analytical classifier to the analytical tissue section may be accepted as trustworthy only when both the control sample data from before and after acquiring the spatially resolved mass spectra from the analytical tissue section fit in the reference control sample data.

In various embodiments, jointly preparing the analytical tissue section and the control sample for analysis can include one of freezing and fixing in formalin. Further, jointly preparing the analytical tissue section and the control sample for analysis may include antigen retrieval ("decrosslinking") in order to render access to certain analytes of interest, such as peptides and proteins, which would not be accessible otherwise. On the other hand, lipids would generally not require any special treatment but could be analysed more or less directly from the tissue.

In various embodiments, jointly preparing the analytical tissue section and the control sample for analysis can include applying a layer of matrix substance for matrix-assisted laser desorption/ionization (MALDI), such as α-cyano-4-hydroxycinnamic acid, 2,5-dihydroxybenzoic acid, or sinapinic acid, onto the analytical tissue section and the control sample.

In various embodiments, jointly preparing the analytical tissue section and the control sample for analysis may include subjecting them to an enzymatic digest, such as a tryptic digest or glycan digest, which substantially preserves spatial distribution.

In various embodiments, the reference control mass spectra can be obtained repeatedly from different batches of reference control samples over time, and any multivariate feature variations manifest therein may be mathematically aligned or projected onto each other. This course of action allows the tracking of multivariate feature drifts in the control sample over time, if any.

BRIEF DESCRIPTION OF THE DRAWINGS

The invention can be better understood by referring to the following figures. The elements in the figures are not necessarily to scale, emphasis instead being placed upon illustrating the principles of the invention (often schematically).

DETAILED DESCRIPTION

While the invention has been shown and described with reference to a number of different embodiments thereof, it will be recognized by those skilled in the art that various changes in form and detail may be made herein without departing from the scope of the invention as defined by the appended claims.

Figure 1:
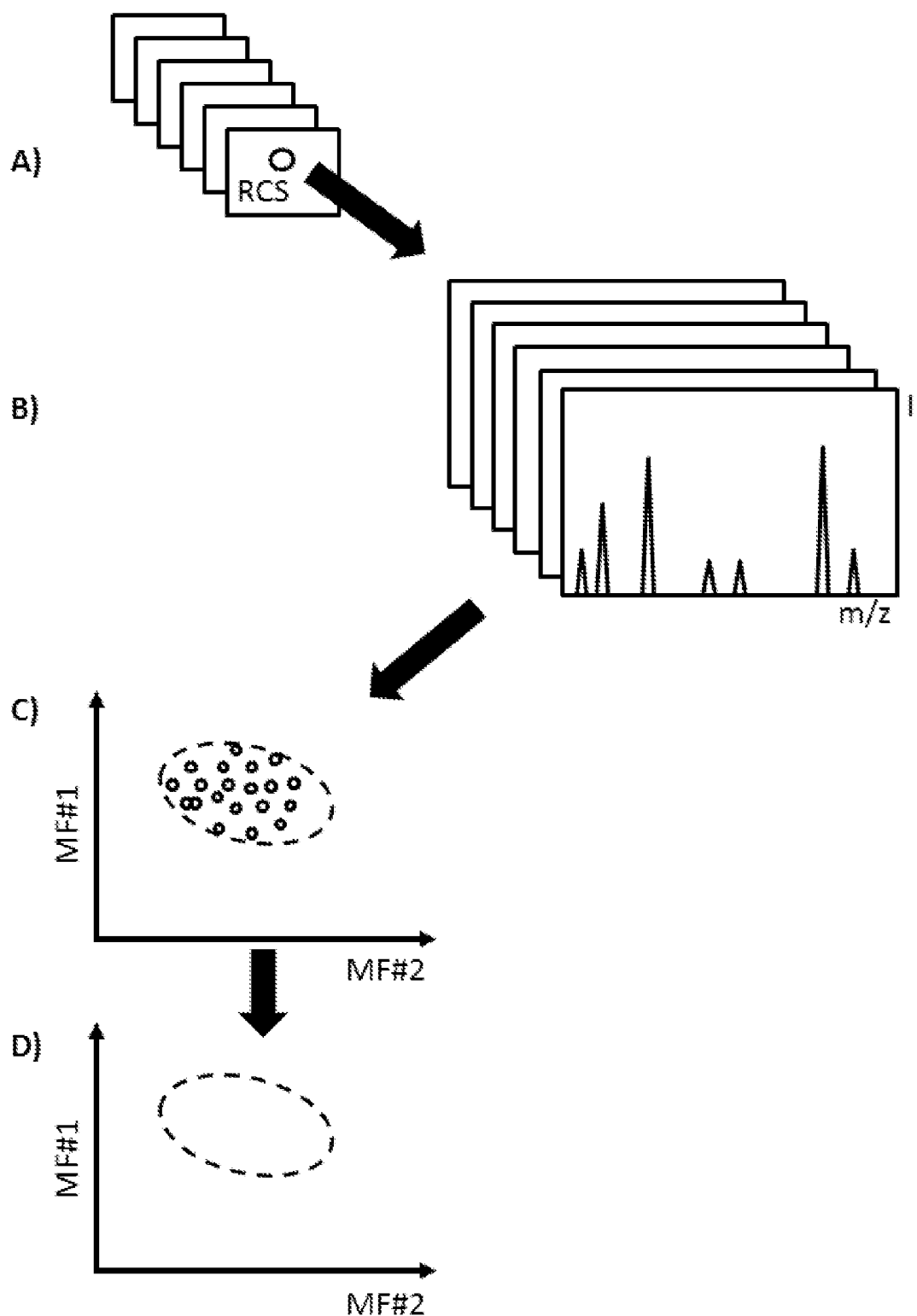
FIG. 1 shows a schematic of a first part of a basic method according to principles of the invention.

A basic method of improving MSI sample preparation workflow monitoring can proceed as illustrated in FIG. 1 for an exemplary generation of a result set of a multivariate feature analysis being used to define an acceptance criterion (statistical model approach).

Step A): Several reference control samples (RCS) of same tissue configuration are prepared on sample supports, preferably under slightly varying conditions, such as using different batches of the same chemical reagent(s) or different embodiments of a particular instrument type or model that may show variations in the calibration, such as incubation chambers, dispensers for MALDI matrices and so on. In so doing, all reference control samples are processed through substantially the same sample preparation protocol and measured in a mass spectrometer, such as a time-of-flight mass spectrometer (qTOF, OTOF, etc.), using predetermined instrumental settings. For the sake of completeness, it is mentioned that mass analysers using other principles than time-of-flight could be used for acquiring the mass spectra, such as Fourier Transform Ion Cyclotron Resonance (FT-ICR) mass spectrometers, Kingdon type mass spectrometers (e.g. the Orbitrap® from Thermo Fisher Scientific Inc.), quadrupole ion traps and mass filters, such as triple quadrupole mass filter assemblies. Those of skill in the art will appreciate that the present disclosure shall not be limited to any particular mass analyser in this regard.

Preferably, a suitable (reference) control sample consists of at least one small piece of tissue with little or ideally no spatial structure. The (reference) control sample can also contain more than one tissue type, but at least one of the tissue types should ideally have no spatial structure. Tissue with little spatial structure at the scale of commonly used MSI pixel sizes of between 1 and 100 micrometers are, for example, liver or muscle sections from rodents.

Advantageously, the tissue in question used for the (reference) control sample should be available in virtually unlimited quantities at a consistent quality. The most probable choices for good tissue for this purpose are either organs from inbred rodents kept under standardized conditions or tissue surrogates prepared from cultured cells. Such cultured cells can be suspended and spun (or otherwise compressed) into pellets that are subsequently processed similar to the analytical tissue section to be investigated, for example, by freezing or chemical fixation, such as formalin fixation, and then slicing them for obtaining the flat specimens. If later batches of the tissue used as the reference control samples show slightly different mass signal characteristics than the batches originally used, it is possible to use a mathematical transformation to align or project the regions of the multivariate feature space defined by spectra measured from the new batches onto those of the old batches. Preferably, a sufficient number of measurements is performed with reference control samples from the old batches measured alongside reference control samples from the new batches to ensure consistency.

Step B): Reference control mass spectra are acquired from the different reference control samples which each (should) show substantially the same mass signal profile characteristic for the particular tissue in the reference control samples. The mass signal profile may vary slightly due to purposely varied preparation conditions in order to account for every-day situations in a laboratory where slight variations in the workflows may also occur, thus making sure that the acceptance criterion is not too narrow and remains yet meaningful.

Step C): The reference control mass spectra acquired from the reference control samples can now be used to define an acceptance criterion (dashed ellipse) derived from a multivariate feature analysis, which criterion in the case depicted draws a tight boundary around the cluster of individual analysis results (hollow circles). For simplification, only two dimensions (multivariate features: MF #1 and MF #2) of the multidimensional space derived from the data in the reference control mass spectra are displayed. The presented course of action could however be easily generalised to a feature space with more dimensions, such as n dimensions where n=2, 3, 4, 5, . . . . In certain (though rather unlikely) cases, it may also be possible to base the characteristic mass signal profile on a single feature, such as the presence or absence of a single mass peak in the reference control mass spectra (n=1).

Step D): The said acceptance criterion is stored for future use. Instead of storing merely the data derived from the reference control mass spectra, such as the acceptance criterion, it would also be possible to store additionally or alternatively the original reference control mass spectra (or at least a representative subset thereof), for example, if it is intended to subject a newly acquired control sample mass spectrum together with the reference control mass spectra to a multivariate feature analysis jointly (see FIG. 3 further below).

Figure 2:
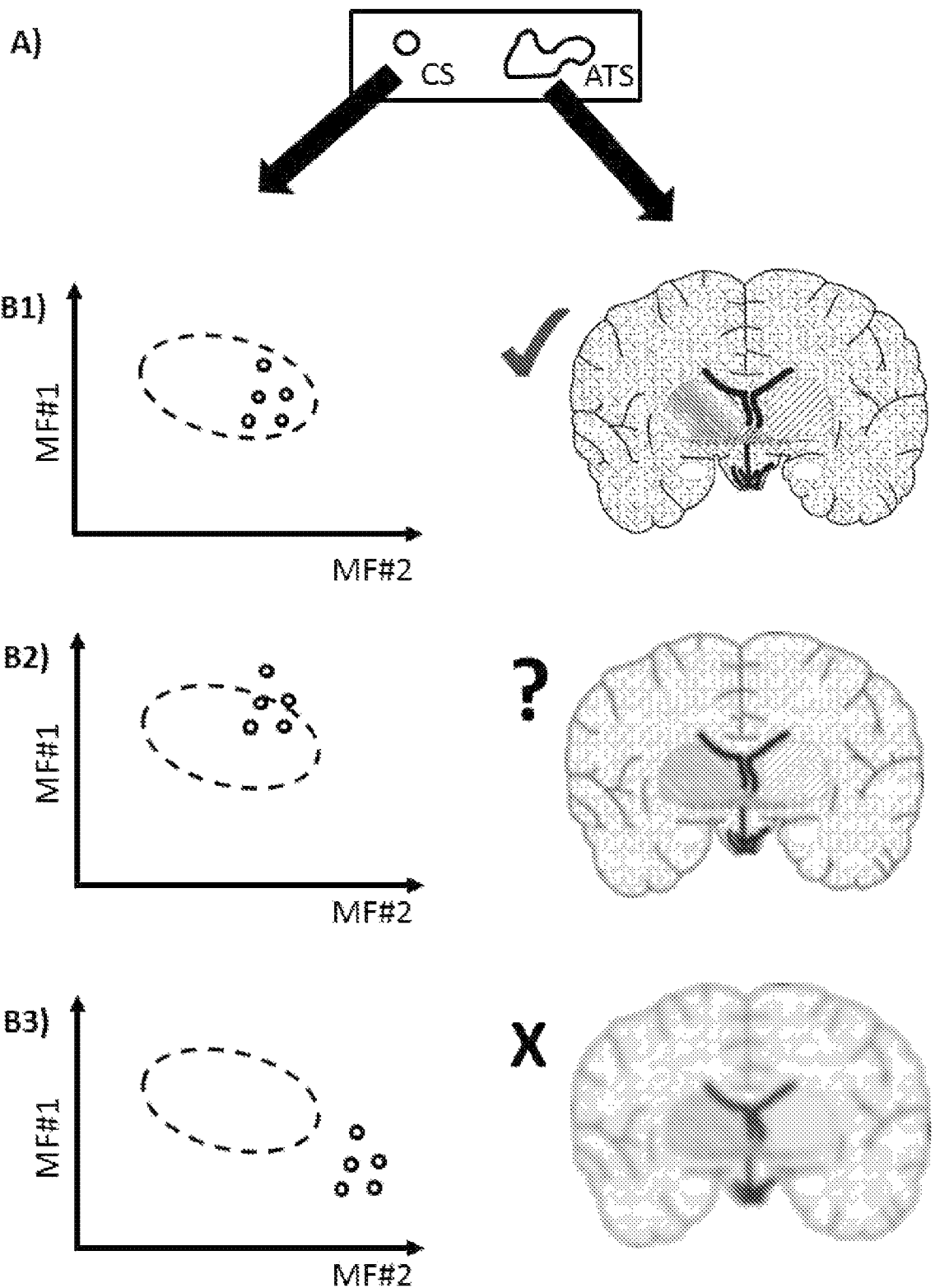
FIG. 2 continues the schematic of the basic method from FIG. 1 by presenting a second part.

FIG. 2 shows an exemplary quality monitoring workflow.

Step A): The analytical tissue section (ATS) of (largely) unknown analyte composition, whose mass spectrometric image is to be determined, is prepared together with a control sample (CS) on the same sample support, which control sample comprises the same type of reference material as in the previous measurements for the reference control mass spectra and the acceptance criterion (FIG. 1). They are processed together through the sample preparation, which encompasses substantially the same conditions as before during the acquisition of the reference control mass spectra, and measured together in the mass spectrometer. Whereas the simultaneous acquisition of spatially resolved mass spectra of the analytical tissue section (ATS) results in a spatial mapping of one or more analytes of interest, exemplified here by a brain section showing different areas, and/or a tissue type classification in particular regions of interest, the investigation of the parallel control sample can in principle lead to the three following scenarios.

Scenario B1): The current multivariate feature analysis results fit well into the acceptance region established previously on the basis of measurements from the same type of control sample (FIG. 1), in which case the mass spectrometric image of the parallel measured analytical tissue section can be labelled as good quality or trustworthy (√).

Scenario B2): The current multivariate feature analysis results fall partly inside and partly outside the acceptance region so that it is not possible to either straightforwardly reject or accept them, in which case the quality of the parallel mass spectrometric image has to be tagged as moderately trustworthy or questionable at least (?). If very strict criteria are applied, such scenario may however also be regarded as a failed quality test.

Scenario B3): The current multivariate feature analysis results are clearly outside the acceptance region so that the mass spectrometric image has to be flagged as untrustworthy or bad quality in any case (X).

It goes without saying that depicting the exemplary brain sections through the scenarios B1) to B3) with increasing degrees of blurring as a function of proximity of the current multivariate feature analysis results to the set of acceptance criterion-defining multivariate feature analysis results has been chosen by way of illustration only. The degrading quality of the analytical tissue section that may be a result of unforeseen variations in the sample preparation process can manifest itself in a different way, such as fading analyte signals, decreasing signal-to-noise ratios and the like.

Figure 3:
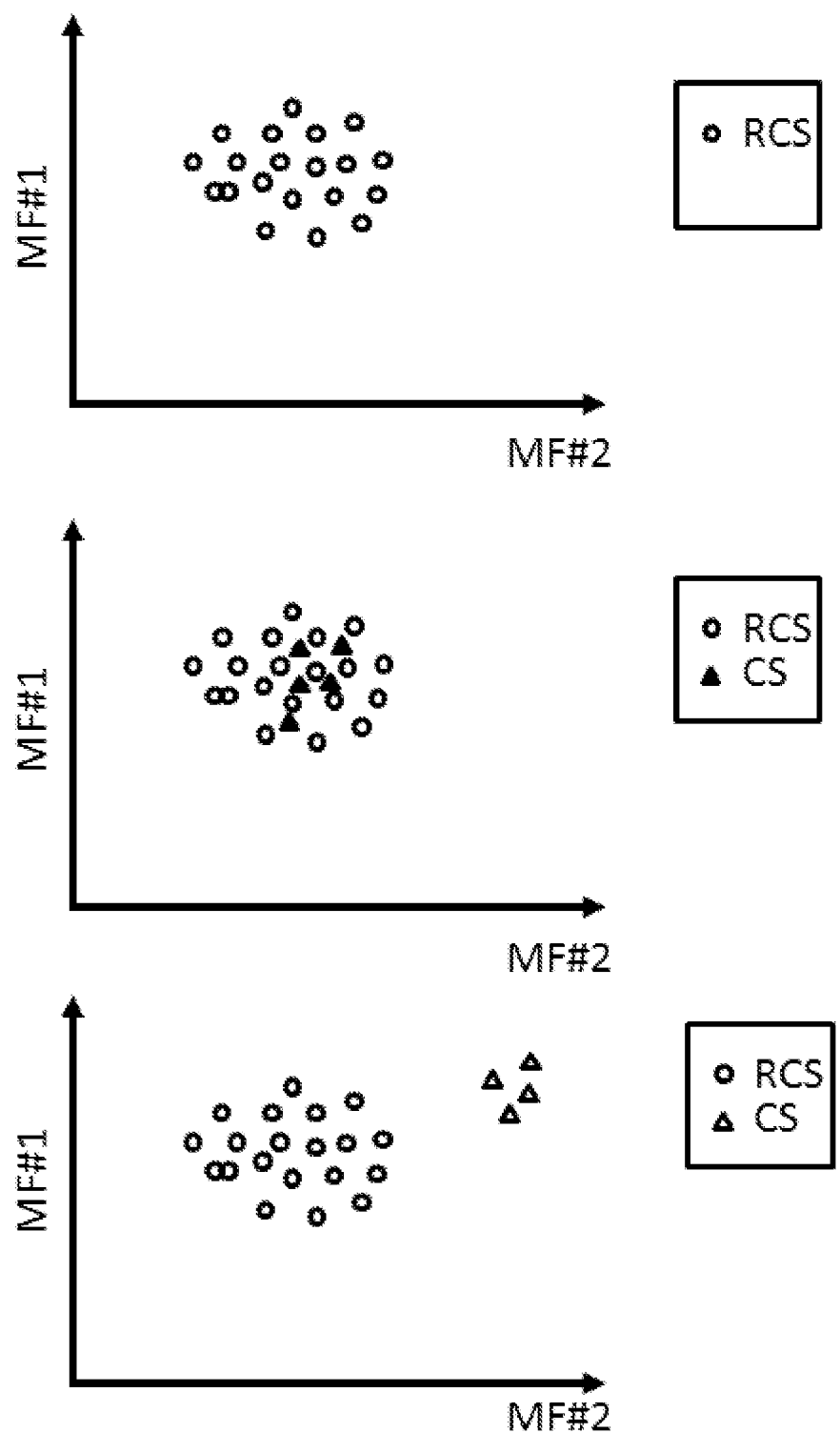
FIG. 3 presents an alternative to the second part as illustrated in FIG. 2.

FIG. 3 depicts an alternative quality assessment workflow (concurrent analysis approach): Rather than defining an acceptance criterion or quality criterion for testing the reference control samples as a statistical model, it is also possible to use the original reference control mass spectra from the reference control measurements (upper panel), see step C of FIG. 1. These can then be subjected to a direct comparison with the control sample spectra (CS) taken from the control sample currently under investigation and measured alongside the analytical tissue section(s) of unknown analyte composition.

The centre panel shows a situation where the control sample measurement under investigation fits well into the feature space region established by the previously acquired reference control data. In such case, there is no indication that the sample preparation workflow has been defective or anomalous, and the parallel measurement of the analytical tissue section(s) and the images produced therefrom can be tagged as trustworthy or good quality in this regard. The bottom panel, on the other hand, illustrates a scenario where the control measurements under investigation come to lie outside the region of acceptance giving rise to the assumption that something detrimental or at least unexpected occurred during the processing of the samples, as a result of which the associated analytical tissue measurement(s) can be tagged as questionable or even untrustworthy. Rather than using all reference control mass spectra for this purpose, as implied above, for the sake of calculation time it is also possible to limit the number to a sufficiently large, randomly-chosen subset.

Not shown in FIG. 3 is a scenario where the multivariate feature cloud of the control sample mass spectra currently under investigation results not in a subset of the reference control sample cloud but part partly overlaps therewith. As has been described before, such situation can lead to a labelling as moderately trustworthy, questionable or, if very strict standards are applied, also untrustworthy.

Going a step further from this afore-described basic method, skilled practitioners in the field of MSI will appreciate that most diagnoses in pathology are differential diagnoses. An example of such differential diagnosis would be the positive or negative classification of the status of the human epidermal growth factor receptor 2 ("Her2") for breast cancer in regions of interest from an analytical tissue section, see for example U.S. Pat. No. 9,164,098 B2 the disclosure of which is herewith incorporated by reference in its entirety. Such classifications have an influence on the subsequent diagnostic steps and/or treatment of the patient so that their quality is of high importance.

Figure 4:
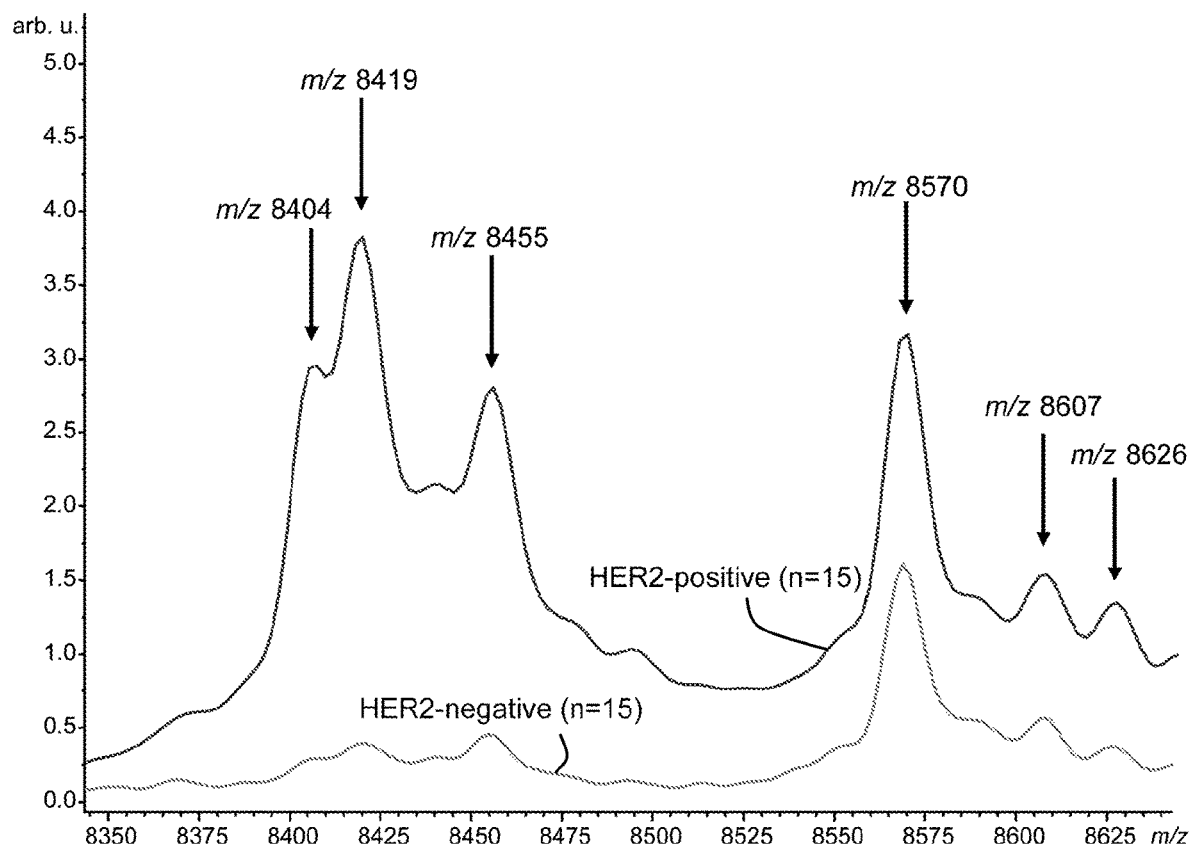
FIG. 4 shows possible classifier mass signals for differential diagnosis of breast cancer tissue based on mass peaks in the range between m/z 8345 to 8640 known from the prior art.

FIG. 4 shows by way of example averaged MALDI-TOF mass spectra of Her2-positive (n=15) and Her2-negative (n=15) breast cancer tissues (discovery set) in the mass range of m/z 8345 to 8640 from the disclosure of U.S. Pat. No. 9,164,098 B2. The arrows mark six peaks with significant differences between the Her2-positive and Her2-negative groups with centroid masses at m/z 8404, 8419, 8455, 8570, 8607, and 8626 indicating their suitability, either individually or combined, as biomarkers when trained on specimens of a specific tissue type.

Other examples of differential diagnosis include R. Casadonte et al., Proteomics 2014, 14, 956-964, where multitissue paraffin blocks have been investigated by MALDI MSI for special tumour types and identification of predictive patterns that could discriminate metastatic breast from pancreatic carcinoma, as well as S. Steurer et al., Int. J. Cancer: 133, 920-928 (2013), where MALDI MSI has identified m/z signals associated with TMPRSS2-ERG gene fusion in a prostate cancer tissue microarray based on patient samples. All of these exemplary publications shall be incorporated herein by reference in their entirety.

If such a differential diagnosis shall be done with MSI data, then a simple library approach as described in the introduction for bacterial identification does not work. Rather statistical approaches are used that involve machine learning. In these approaches training data with a known class membership are used. A statistical model is then created that tries to find characteristic differentiating properties between the training spectra of the different known classes in the background of the usual technical and biological variation in the data. To classify unknown spectra, such as telling diseased tissue from healthy tissue or different types of diseased tissue in regions of interest from a mass spectrometric image, this model is then used to predict the class membership of the unknown spectra. Models that can be used for this purpose are principal component analysis based models, linear discriminant analysis, support vector machines, genetic algorithms, neuronal networks, decision trees, or random forests.

The said algorithms are all multivariate techniques. Mass spectra are seen as multivariate data, at the lowest level as a vector of individual data points as they are detected by the digitizer of the mass spectrometer. Since these data points are not independent from each other, but several data points together describe mass spectrometric signals, commonly a feature detection is performed that detects the mass spectrometric signals and reduces the information to just the information on the detected signals. One possible way of doing this is described in U.S. Pat. No. 6,288,389 B1 the disclosure of which is incorporated herein by reference in its entirety. Such "peak detection" or "peak picking" is not strictly necessary for the following explanations, but may be beneficial and is therefore commonly done.

All the features of the mass spectrum span a multivariate feature space, with each feature defining one coordinate in that space. Each mass spectrum of the training data set then occupies one distinct point in that multivariate space. During the training of the classifier, that multivariate space is partitioned in a way to allow the separation of the different classes of the training data. For the classification of an unknown spectrum, or in other words, the test whether characteristic mass features that have been found previously to be indicative of a particular tissue state are present in the unknown spectrum currently under investigation, this spectrum is projected in the same multivariate space, and it is checked in which partition of the space the spectrum is located. The spectrum is then classified accordingly.

The algorithms used, such as a linear discriminant analysis, can partition the whole feature space. In this case the space is projected in a way so that features that favour the discrimination of the training data are given high weight and features that do not contribute to the differentiation are given low weight. In other cases, a subspace of the original feature space will typically be used that is only based on features that do support the differentiation of the training classes; all other features are then disregarded.

The commonly used algorithms for classification partition the whole multivariate space, and for that reason will always force a classification of any mass spectrum that they are applied to, even if the spectrum to be classified bears no similarity to the originally used training data. This can lead to different sorts of perceived or actual false classifications, which are undesirable for a diagnostic procedure. The following types of apparent or actual false classifications are possible:

(i) Classification applied to false tissue type: If the classifier is applied to spectra from a tissue type that was not used for the training of the classifier, then a classification to one of the classes used for training will result nevertheless, even if the tissue types are unrelated. This may appear to the average observer as a false classification, but it is not. It is rather a result of applying a statistical model to a question it was not originally trained for. In the case of diagnosis of tissue, it would be the responsibility of the pathologist to ensure that the classifier is only applied to the correct question.

(ii) Problem with the sample: There are some influences of the pre-analytical handling of the sample that cannot always be controlled but that may have an effect on the shape of the mass spectral profile nevertheless. In the case of formalin-fixed samples, this could for example be a tissue specimen that is so large that it was not completely penetrated by the formalin. In such case, mass spectrometric signals may appear in areas where they were not seen before, or peak intensities may be grossly altered. In this case, the classifier may be applied to the right classification problem, but it still might be classified to the wrong class. Since the classifiers lose information on the original shape of the mass spectrometric signals to either give low emphasis or completely ignore features that do not contribute to the classification, they cannot detect if the spectral shape is different. To overcome this problem it is necessary to independently apply known methods that can tell if the spectra to be classified have high enough overall similarity with the training data.

(iii) Variation in the analytical performance of the workflow: Preparation of samples for mass spectrometric imaging can involve many steps. These may include antigen retrieval, an enzymatic digest of the tissue to release peptides or other analytes, the application of a matrix layer in case of MALDI and of course the measurement in a mass spectrometer. The following publications illustrate by way of example the individual steps in sample preparation for MSI quite neatly: FIG. 1 in K. Gorzolka et al., Histology and Histopathology 19 May 2014, 29(11), 1365-1376; and FIG. 2 in A. Ly et al., Nature Protocols, 11, 1428-1443 (2016). Unexpected variations in all of these steps, such as by using different batches of chemical reagents or different embodiments of the same instruments whose calibrations can deviate slightly, may lead to changes in the mass spectrometric profiles or in intensity ratios used for the classification. These variations may go unnoticed. In such a case, the classifier might be applied to the right question and to the right sample but still give a false classification.

Since changes in the analytical workflow in MSI can have an effect on the shape of the mass spectrometric profiles, they can lead to false classifications in a classification-based analysis. It is not possible to verify the analytical integrity of the entire workflow from sampling, such as cutting slices from a tissue block, through sample preparation to mass spectrometric measurement and classification solely based on the shape of the mass spectrometric profile or the sample to be classified. This is mainly due to the fact that these samples are of (largely) unknown analyte composition, and there are various reasons why results could be interpreted to indicate a problem with the analytical workflow even if there is none. There is also the possibility that the difference between the training spectra of the classes is very small, and a shift in preparation or measurement conditions could push spectra across the classification boundary. In such case, the mass spectra could be sufficiently similar to the training data and yet result in a wrong classification.

For all these reasons, it is advantageous to judge the analytical integrity of the workflow against a (preferably homogenous) control sample with well-known and characterised mass spectrometric profile.

A control sample can be prepared next to each sample that is used for generating the training data for the classifier as well as analytical tissue section of unknown analyte composition to be classified. It is also possible to provide a mass spectrometric sample support as a consumable that already carries such a control sample as a ready-for-use kit-of-parts.

The control sample is then processed together with the analytical tissue section on the same sample support through the entire analytical workflow from preparation until mass spectrometric measurement so that, in a kind of tell-tale approach, the same deviations and aberrations therein, if any, will precipitate somehow in the mass features of the control sample.

The general scheme of a diagnostic workflow from generating the classifier to the diagnostic application of the classifier may be as follows.

In a first step, the training samples are processed together with the same type of reference control sample for each individual measurement of the training cohort. The data from the training samples are used to build the classifier, such as for Her2-positive and Her2-negative status or any other suitable diagnostic target. The reference control mass spectra from the reference control samples are kept to later define a region in the feature space for the (reference) control sample that can be used to compare spectra from current control samples measured together with analytical tissue sections to be investigated with the classifier.

When an analytical tissue section is classified, the same type of control sample as before is measured next to it as described above. The classifier is applied to the analytical tissue section and results in a classification which may distinguish certain areas of the analytical tissue section(s) from their surroundings. The control sample from the same measurement is compared with the reference control mass spectra from the reference control samples measured during the generation of the classifier. If the current control sample belonging to the measurement of the analytical tissue section is similar enough to the original reference control measurements, then the classification is scored as trustworthy or good quality, otherwise it can be labelled as untrustworthy or bad quality.

Depending on the measure used to calculate the distance in the multivariate feature space, there may also be a more detailed scale for the trustworthiness of the classification of the analytical tissue section of unknown composition, such as "highly trustworthy", "moderately trustworthy", "questionable" and "not trustworthy". Even a continuous score can be considered. Such a scoring scheme could guide the pathologist to use additional methods of diagnosis to come to a final diagnosis. Since both the reference control measurements from the classifier generation and the spatially resolved mass spectra from the analytical tissue section contain multiple mass spectra, it is also possible that some mass spectra from the control sample measured alongside the analytical tissue section comply with an acceptance criterion and some do not. The trustworthiness (quality) score may also reflect the percentage of spectra that are allowed to fall out of the confidence/acceptance region, as indicated in scenario B2 of FIG. 2 for instance.

There are several possibilities how the similarity of the (reference) control measurements to each other can be determined. A simple possibility is the setting-up of a statistical model using a single-class support vector machine or a (kernel) density estimator. The reference control mass spectra are then subjected to a multivariate feature analysis separately in order to define the criteria for the statistical model, and it is checked if the results of the same multivariate feature analysis for the control mass spectra currently under investigation comply with this statistical model. In an additional or alternative embodiment, one can also perform a principal component analysis of the original reference control measurements (or a representative subset thereof to speed up the calculation) together with the new data and check whether the two types of spectra fall into the same multidimensional region of the feature space (analogous to FIG. 3). A similar approach can be done by clustering approaches, such as k-means or hierarchical clustering of the reference control data with the new data, either with a preceding principal component analysis or without.

Outside the field of mass spectrometry imaging, Petricoin and co-workers (Petricoin et al., The Lancet • Vol 359 • Feb. 16, 2002, 572-577) have described a related approach for finding outliers in a classification of diseased sera. However, they have done the similarity measurement only on the subspace of the original feature space that was used to build the classifier. This approach is therefore unable to see major dissimilarities between training data and data to be classified that appear in other regions of the spectra.

Aside from the assessment of multivariate similarity between the reference control measurements of the training dataset and the control measurement of the spectra to be classified, the data can also be used to establish and assess other quality criteria that can allow an assessment of the quality of the mass spectra and the performance of the mass spectrometer. These can include measures such as a central tendency of the number of mass spectrometric signals above certain intensity or signal-to-noise thresholds, acceptable ranges of intensity drifts during the measurements, the shape of the histogram or density of the distribution of the total ion count, the intensity variation of spectra or individual mass signals in neighbouring pixels.

Since there is a possibility that some technical change or defect occurs during a longer MSI measurement, which can well take up to twelve hours or even more, there is also the possibility of measuring part of the control sample prior to the analytical tissue section (to be classified) and part of the control sample thereafter. A dataset would then be only accepted for showing a reliable analyte distribution (image) or classification, if both the control sample data from before and after the measurement of the unknown analytical tissue section pass the quality check with the reference control measurements.

Figure 5:
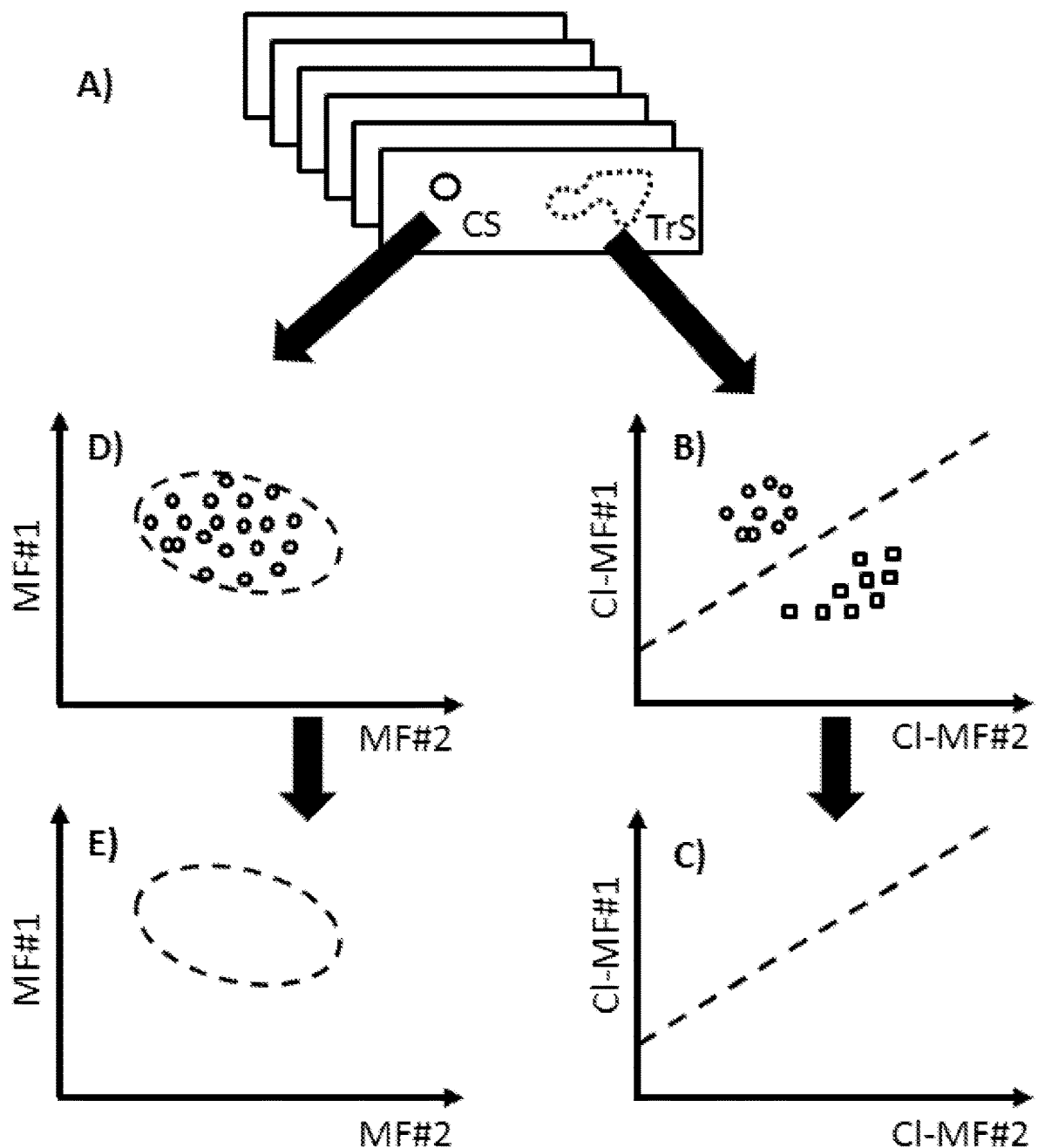
FIG. 5 shows a schematic of a first part of a monitoring workflow using control samples and comprising classifier training.

In view of the foregoing explanations, a possible way of improving mass spectrometry imaging sample preparation workflow monitoring for differential diagnosis can proceed as illustrated in FIG. 5 for an exemplary generation of a classifier and reference control data.

Step A): The samples with the training cohort (TrS) of known tissue type and known classifier status are prepared together with the control samples (CS) on the same sample support. They are processed together through the sample preparation and measured together in the mass spectrometer to yield reference control mass spectra and corresponding classifier training mass spectra (not shown).

Step B): The multivariate feature analysis results from the spectra of the training classes (indicated by squares and circles) are used to generate a classifier (dashed diagonal line). For simplification, only two dimensions of the multidimensional space (classifier multivariate features: CI-MF #1 and CI-MF #2) derived from the data in the spectra are displayed. The presented course of action could however be easily generalised to spaces of higher dimension.

Step C): For future use with the same type of tissue on which it was identified, this classifier is stored.

Step D): The reference control mass spectra from the control samples are again used to define an acceptance criterion (dashed ellipse) in a statistical model approach, as has been set out before.

Step E): This acceptance criterion is stored for future use with the same type of control tissue on which it was found.

Figure 6:
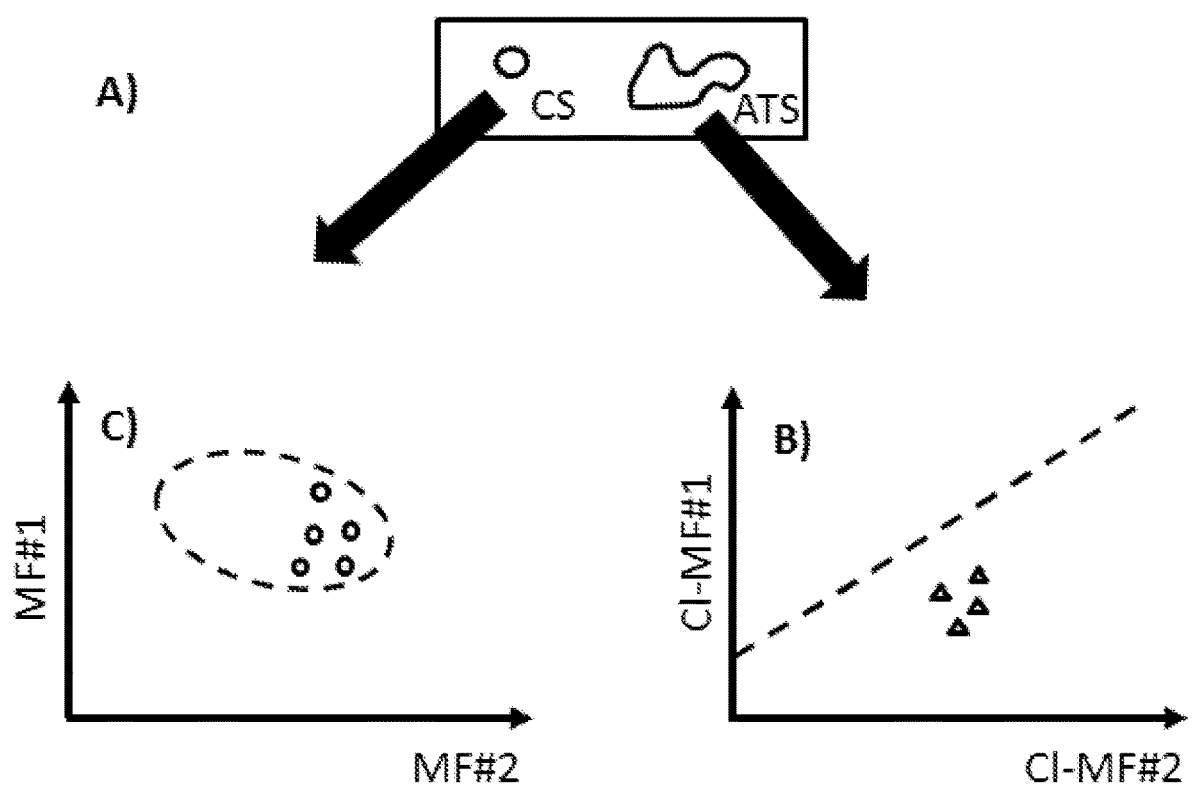
FIG. 6 continues the schematic of the monitoring workflow from FIG. 5 by presenting a second part comprising actual classifier application.

FIG. 6 now illustrates an exemplary classification workflow which uses the measurements and definition as previously found.

Step A): The analytical tissue section (ATS) of unknown analyte composition which comprises the same tissue type as the training cohort is prepared together with the control sample (CS) which comprises likewise the same type of reference control material on the same sample support. They are processed together through the sample preparation and measured together in the mass spectrometer.

Step B): The spatially resolved mass spectra from the analytical tissue section, the multivariate features of which are indicated by triangles, are subjected to classification with the classifier from steps A) to C) of FIG. 5, and yield a clear classification result. In some instances, the classifications result could also be inconclusive, for instance, when the multivariate features clusters transcend the borderline between different classes (scenario not shown here).

Step C): The spectra from the control sample are subjected to a matching with the acceptance/quality criterion from steps A), D) and E) of FIG. 5. Based on the result from this, it is then decided whether or not the classification result of the analytical tissue section can be trusted or not. As has been mentioned before, instead of using a statistical model as a result of a separate multivariate feature analysis, the mass spectra from the current control sample and those from the reference control samples could undergo the multivariate feature analysis jointly, as explained with reference to FIG. 3.

Particular emphasis has been put in the above description on MALDI mass spectrometric imaging of FFPE tissue sections. Those of skill in the art will understand, however, that the principles of the present disclosure can be equally applied to other sample types, such as frozen tissue sections, and other ionization techniques, such as desorption electrospray ionisation (DESI) and secondary ion mass spectrometry (SIMS) to name but a few.

Generally, the invention has been shown and described above with reference to a number of different embodiments thereof. It will be understood, however, by a person skilled in the art that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims, including any equivalent implementations, as the case may be.

The invention claimed is:

1. A method for monitoring a quality of sample preparation workflows of an analytical tissue section for mass spectrometric imaging, comprising:
   providing a sample support suitable for mass spectrometric imaging;
   depositing the analytical tissue section and a control sample on the sample support;
   jointly preparing the analytical tissue section and the control sample for analysis under predetermined conditions;
   acquiring mass spectra from the control sample and acquiring spatially resolved mass spectra from the analytical tissue section in a same measurement run;
   subjecting the mass spectra of the control sample to multivariate feature analysis;
   ascertaining if a result of the multivariate feature analysis fits into a range of outcomes established by subjecting a set of reference control mass spectra, which are obtained from control samples of a same type that have been prepared under substantially the same predetermined conditions, to the same multivariate feature analysis; and
   tagging a mass spectrometric image produced from the spatially resolved mass spectra of the analytical tissue section with a result of the ascertaining.

2. The method of claim 1, further comprising using substantially homogeneous tissue as the control sample.

3. The method of claim 1, wherein at least one of a kidney section, liver section, muscle section and a section from a tissue surrogate comprising cultured cells is used as the control sample.

4. The method of claim 1, wherein the multivariate feature analysis of the mass spectra from the current control sample and the reference control mass spectra is carried out one of separately and jointly, and the ascertaining comprises checking if the results of the multivariate feature analysis fall into a same region of a multivariate feature space.

5. The method of claim 4, wherein the separate multivariate feature analyses encompass using at least one of a single-class support vector machine and density estimator.

6. The method of claim 4, wherein the joint multivariate feature analysis encompasses using at least one of principal component analysis, k-means clustering and hierarchical clustering.

7. The method of claim 4, wherein the joint multivariate feature analysis employs a randomly chosen subset of the reference control mass spectra in order to shorten calculation time.

8. The method of claim 1, wherein the predetermined conditions under which the control samples of the same type for the reference control mass spectra have been prepared comprise using different batches of same chemical reagents and different embodiments of a same instrument type or model.

9. The method of claim 1, wherein the predetermined conditions comprise exposure to at least one of liquid and wet chemistry.

10. The method of claim 1, wherein a first portion of the mass spectra from the control sample is acquired before the acquisition of the spatially resolved mass spectra from the analytical tissue section and a second portion of the mass spectra from the control sample thereafter, and wherein the mass spectrometric image is accepted as trustworthy only when both the control sample data from before and after acquiring the spatially resolved mass spectra from the analytical tissue section fit in the reference control sample data.

11. The method of claim 1, further comprising obtaining the reference control mass spectra from control samples of the same type which are measured alongside training tissue sections each prepared together with the corresponding control sample on a same sample support, wherein the measurements from the training tissue sections are used to define a tissue-specific analytical classifier based on characteristic mass signal profiles.

12. The method of claim 11, wherein the analytical classifier is applied to the spatially resolved mass spectra from the analytical tissue section of the same tissue type as the training tissue sections.

13. The method of claim 11, wherein defining the analytical classifier comprises using at least one of principal component analysis based models, a linear discriminant analysis, support vector machines, genetic algorithms, neuronal networks, decision trees, and random forests.

14. The method of claim 1, wherein jointly preparing the analytical tissue section and the control sample for analysis includes one of freezing and fixing in formalin.

15. The method of claim 14, wherein jointly preparing the analytical tissue section and the control sample for analysis includes antigen retrieval.

16. The method of claim 1, wherein jointly preparing the analytical tissue section and the control sample for analysis includes applying a layer of matrix substance for matrix-assisted laser desorption/ionization (MALDI) onto the analytical tissue section and the control sample.

17. The method of claim 1, wherein jointly preparing the analytical tissue section and the control sample for analysis includes subjecting them to an enzymatic digest which substantially preserves spatial distribution.

18. The method of claim 17, wherein the enzymatic digest is a tryptic digest or glycan digest.

19. The method of claim 1, wherein the reference control mass spectra are obtained repeatedly from different batches of reference control samples over time, and any multivariate features variations manifest therein are mathematically projected onto each other.

20. The method of claim 1, wherein the tagging comprises tagging the mass spectrometric image as "trustworthy" when the multivariate feature analysis result fits well into an acceptance region established previously on the basis of measurements from a same type of control sample, tagging the mass spectrometric image as "moderately trustworthy/questionable" when the multivariate feature analysis result falls partly inside and partly outside the acceptance region so that it is not possible to either straightforwardly reject or accept it, and tagging the mass spectrometric image as "untrustworthy" when the multivariate feature analysis result is substantially outside the acceptance region.

* * * * *